United States Patent
Huang et al.

(10) Patent No.: US 9,114,246 B2
(45) Date of Patent: Aug. 25, 2015

(54) SPINAL NERVE STIMULATION RINGS FOR REHABILITATION OF PATIENTS WITH SPINAL TRAUMA AND STROKE

(71) Applicant: University of Rochester, Rochester, NY (US)

(72) Inventors: Jason Huang, Rochester, NY (US); Samantha Dayawansa, Rochester, NY (US)

(73) Assignee: University of Rochester, Rochester, NY (US)

( * ) Notice: Subject to any disclaimer, the term of this patent is extended or adjusted under 35 U.S.C. 154(b) by 291 days.

(21) Appl. No.: 13/838,180

(22) Filed: Mar. 15, 2013

(65) Prior Publication Data
US 2014/0275718 A1    Sep. 18, 2014

(51) Int. Cl.
*A61N 2/00* (2006.01)
*A61N 1/36* (2006.01)
*A61N 1/05* (2006.01)

(52) U.S. Cl.
CPC ............ *A61N 2/006* (2013.01); *A61N 1/36103* (2013.01); *A61N 1/0556* (2013.01)

(58) Field of Classification Search
CPC . A61N 1/0551; A61N 1/0056; A61N 1/0558; A61N 2/004; A61N 2/006; A61N 2/008
USPC ..................... 600/9–15; 607/43, 48, 117, 118
See application file for complete search history.

(56) References Cited

U.S. PATENT DOCUMENTS

| | | |
|---|---|---|
| 8,788,040 B2 * | 7/2014 | Haessler .......................... 607/39 |
| 2008/0046055 A1 * | 2/2008 | Durand et al. ................. 607/118 |
| 2011/0125203 A1 * | 5/2011 | Simon et al. ...................... 607/2 |

* cited by examiner

*Primary Examiner* — John Lacyk
(74) *Attorney, Agent, or Firm* — Patent Technologies, LLC; Robert D. Gunderman, Jr.

(57) ABSTRACT

A device circles the spinal segmental nerves like a ring and causes stimulation of the nerves. The present invention offers magnetic as well as electric stimulation properties in order to balance the two modes.

14 Claims, 4 Drawing Sheets

SPINAL NERVE STIMULATION RINGS FOR REHABILITATION OF PATIENTS WITH SPINAL TRAUMA AND STROKE

FIELD OF THE INVENTION

The present invention is directed to rehabilitation of patients with spinal trauma and stroke and more particularly to such rehabilitation using stimulation rings.

DESCRIPTION OF RELATED ART

Spinal cord trauma is damage to the spinal cord. It may result from direct injury to the cord itself or indirectly from disease of the surrounding bones, tissues, or blood vessels.

Injuries at any level can cause increased muscle tone (spasticity), loss of normal bowel and bladder control (may include constipation, incontinence, bladder spasms), numbness, sensory changes, pain, weakness, and paralysis. When spinal cord injuries occur in the neck area, symptoms can affect the arms, legs, and middle of the body. The symptoms may occur on one or both sides of the body. Symptoms can also include breathing difficulties from paralysis of the breathing muscles, if the injury is high up in the neck. When spinal injuries occur at chest level, symptoms can affect the legs. Injuries to the cervical or high thoracic spinal cord may also result in blood pressure problems, abnormal sweating, and trouble maintaining normal body temperature. When spinal injuries occur at the lower back level, symptoms can affect one or both legs, as well as the muscles that control the bowels and bladder.

Forms of treatment vary. Corticosteroids, such as dexamethasone or methylprednisolone, are used to reduce swelling that may damage the spinal cord. If spinal cord pressure is caused by a growth that can be removed or reduced before the spinal nerves are completely destroyed, paralysis may improve. Ideally, corticosteroids should begin as soon as possible after the injury.

Surgery may be needed to remove fluid or tissue that presses on the spinal cord (decompression laminectomy); remove bone fragments, disk fragments, or foreign objects; or fuse broken spinal bones or place spinal braces.

Bedrest may be needed to allow the bones of the spine to heal.

Spinal traction may be recommended. That can help keep the spine from moving. The skull may be held in place with tongs (metal braces placed in the skull and attached to traction weights or to a harness on the body). The patient may need to wear the spine braces for a long time.

The patient may need physical therapy, occupational therapy, and other rehabilitation therapies after the injury has healed. Rehabilitation will help the patient to cope with the disability from the spinal cord injury.

Muscle spasticity can be relieved with medications taken by mouth or injected into the spinal canal. Botox injections into the muscles may also be helpful. Painkillers (analgesics), muscle relaxers, and physical therapy are used to help control pain.

However, none of those treatments encourage regrowth of nerve tissue. One form of treatment that is intended to do so is magnetic nerve stimulation. Available magnetic nerve stimulation devices for stimulating sacral nerve roots are indirect. Indirect magnetic stimulation of spinal segments and sacral nerve roots has been shown to promote bowel emptying of patients with spinal cord damage as well as induce enhancement of respiratory function in tetrapegic patients. However, indirect magnetic nerve stimulation has received mixed results, possibly due to its indirectness. There are no existing devices for direct magnetic spinal nerve stimulation.

SUMMARY OF THE INVENTION

It is therefore an object of the invention to provide direct magnetic spinal nerve stimulation.

To achieve the above and other objects, the present invention is directed to a device that circles the spinal segmental nerves like a ring and causes stimulation of the nerves. Electric stimulation of the severed nerve roots has given favorable results. Some reports indicate that magnetic stimulation reduces spasticity. The present invention offers magnetic as well as electric stimulation properties in order to balance the two modes.

The present invention can be utilized for direct stimulation of patients with spinal trauma and stroke. The idea is to simulate anterior roots of the spinal cord segmental nerves related to the movements. Initially, the targeted functions will be bowel emptying, bladder stimulation, and cough induction. If those become successful, a program and a stimulator will be made for all motor functions based on the root involvement of those of limb movements.

The final product will allow a patient to control his/her motor movements using a remote control device. The initial mode of stimulation will be magnetic. If the outcome following magnetic stimulation is minimal reduction of hyperreflexia or spasticity, which is a common side effect following upper motor neuron lesions like spinal cord injury or stroke, magnetic stimulation only will be insufficient to achieve the full motor control. In that case, electronic stimulation through wire electrodes along with magnetic stimulation will be applied. A balance of those two modes of stimulation will control hyperreflexia and spasticity to achieve movements.

A wireless power supply and telemetric control can be provided to avoid infections and minimize the size of the device. Those devices will be implanted microsurgically and will be screwed to the bone using plastic screws.

Stimulating collars can be made out of plastic magnetic conductive material. That approach will allow patients to go through the usual MRI scans, etc.

Immediate applications include the following:
1) Stimulate bowel movements;
2) Stimulate bladder emptying;
3) Stimulate an erection;
4) Reduce muscle spasticity following upper motor neuron lesions; and
5) Induce cough to prevent respiratory infections.

In some possible embodiments, all spinal cord segments will carry rings for individual nerve stimulation, and a software program will stimulate all involved segments in optimum stimulation for motor movement, with the goal of immediate motor control following peripheral nerve lesions.

BRIEF DESCRIPTION OF THE DRAWINGS

A preferred embodiment and variations thereof will be set forth with reference to the drawings, in which.

DETAILED DESCRIPTION OF THE PREFERRED EMBODIMENT

Figure 1:
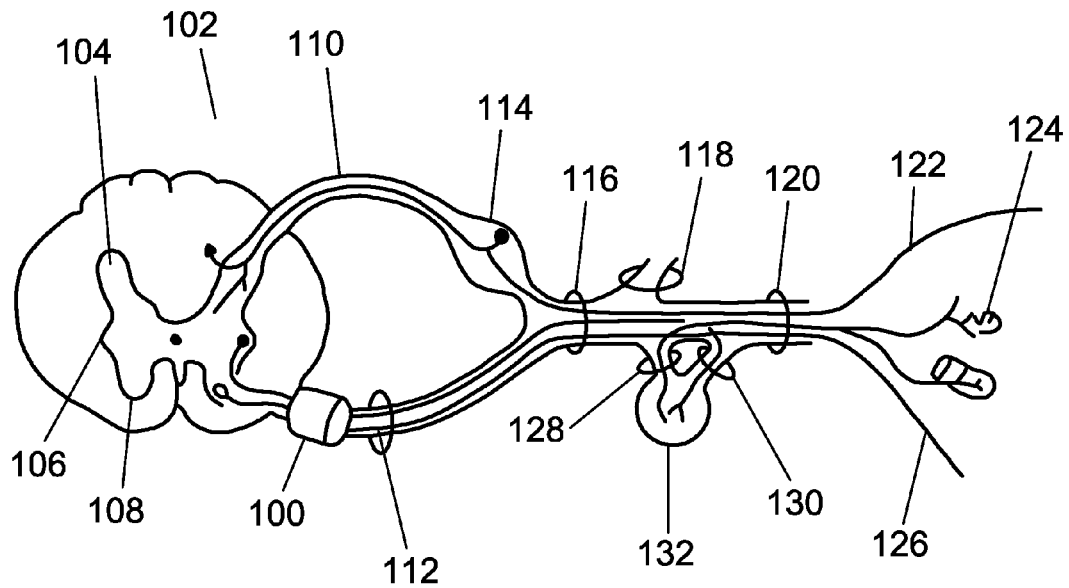
FIG. 1 is a diagram showing the placement of the collar of the preferred embodiment in the patient's nervous system.

A preferred embodiment of the present invention and variations thereof will be set forth in detail with reference to the drawings, in which like reference numerals refer to like elements or steps throughout.

FIG. 1 shows an example of placement of a spinal stimulating collar or ring 100. The spinal cord 102 (shown here in cross section) includes a dorsal (posterior) horn 104 of spinal gray matter; a lateral horn 106, found only in segments T1-L2, of preganglionic sympathetic neurons; and a ventral (anterior) horn 108 containing motor neurons. Dorsal and ventral roots 110, 112 extend from the dorsal and ventral horns 104, 108 respectively. The dorsal root includes a dorsal ganglion 114. The roots 110, 112 join to form a spinal nerve 116, which branches into a dorsal primary ramus 118, which goes to the skin and muscles of the back, and a ventral primary ramus 120, which splits into sensory fibers 122, postganglionic sympathetic innervation (into glands and blood vessels) 124, and motor axons 126 to skeletal muscle. The ventral primary ramus 120 is also connected via a gray ramus communicans 128 and a white ramus communicans 130 to a sympathetic (paravertebral) ganglion 132.

Figure 2:
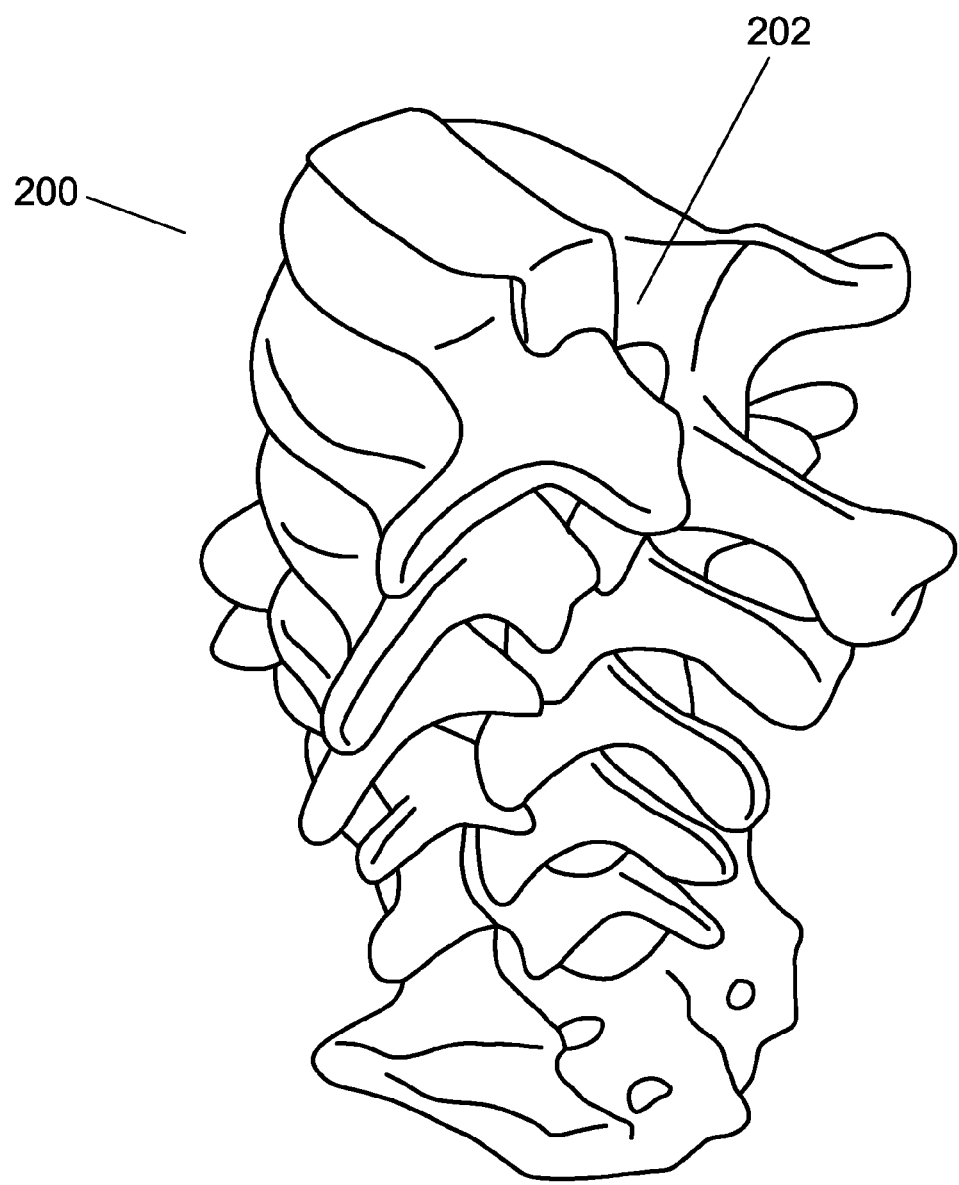
FIG. 2 is a diagram showing the placement of the collar relative to the spine.

The collars 100 surround the ventral nerve roots 112 and are attached to the bone by microscrews or in any other suitable manner. FIG. 2 shows the spine 200 defining the spinal canal 202. The posteriors of the vertebral bodies and the vertebral arches form the bony border of the spinal canal 202. The spinal canal 202 contains the spinal cord 102 and the nerve roots 110, 112. A spinal stimulating collar 100 is attached as shown.

Figure 3A:
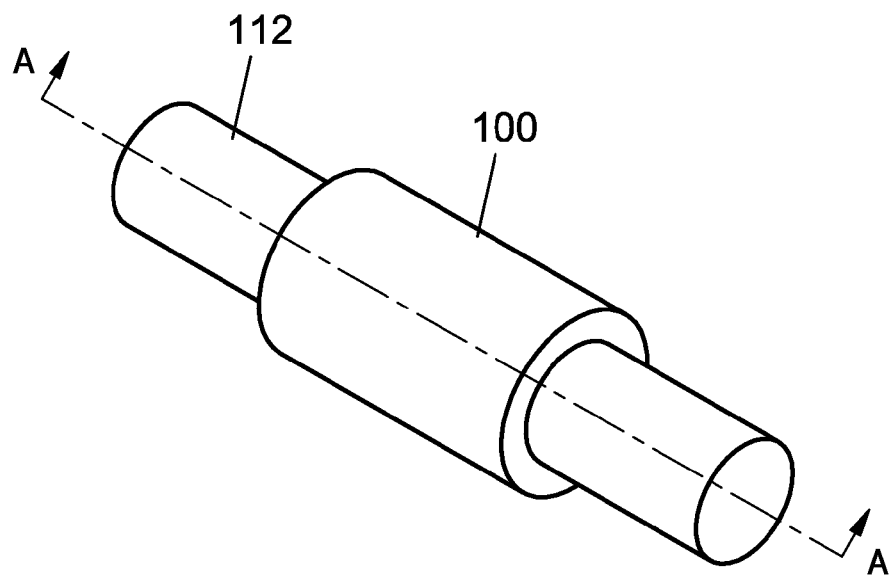
FIG. 3A is a close-up view of the sleeve on a nerve.
Figure 3B:
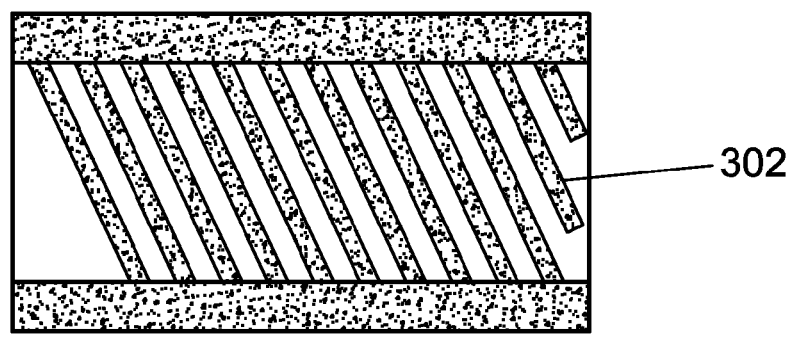
FIG. 3B is a cross-sectional view of the collar.

FIG. 3A shows a collar 100 surrounding a ventral root 112. FIG. 3B shows a coronal section of the collar 100, including stimulating magnetic fibers 302.

Figure 4:
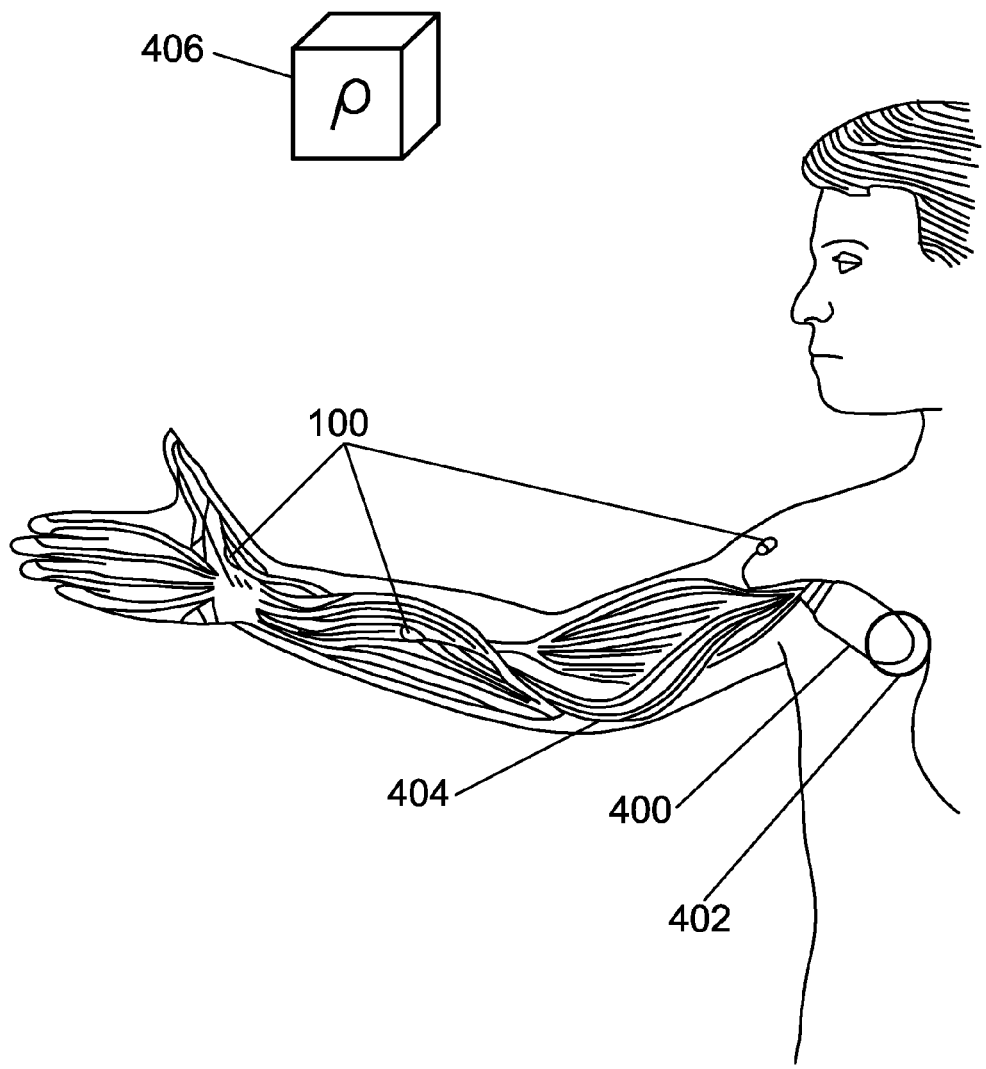
FIG. 4 is a diagram showing an alternative placement of the collar.

FIG. 4 shows the use of the preferred embodiment to surround nerve roots during peripheral nerve repair. An implanted stimulator 400 includes a transmitting coil 402 for control and is connected via electrode leads 404 to collars or rings 100. The coil 402 allows wireless communication with a processor 406 for control. Such a stimulator 400 and processor 406 can be used in any embodiment to provide the correct stimulation.

While preferred embodiments and variations thereof have been set forth in detail, those skilled in the art who have reviewed the present disclosure will readily appreciate that other embodiments can be realized within the scope of the invention. For example, recitations of materials and of the placement of the collar are illustrative rather than limiting. Therefore, the present invention should be construed as limited only by the appended claims.

What is claimed is:

1. A method for applying treatment to a nerve of a patient, the method comprising:
    (a) placing a collar around the nerve;
    (b) applying magnetic stimulation to the nerve through the collar;
    (c) receiving an outcome from the magnetic stimulation; and
    (d) applying electrical stimulation to the nerve based on the received outcome.

2. The method of claim 1, wherein the nerve is a spinal nerve.

3. The method of claim 2, wherein the nerve is a ventral root.

4. The method of claim 1, wherein the received outcome is a reduction in patient hyperreflexia.

5. The method of claim 1, wherein the received outcome is a reduction in patient spasticity.

6. The method of claim 1, wherein the nerve is a peripheral nerve.

7. The method of claim 1, wherein step (b) is performed under telemetric control.

8. A device for applying treatment to a nerve of a patient, the device comprising:
    a stimulating collar capable of being placed around the nerve; and
    a stimulator for applying electrical as well as magnetic stimulation to the nerve through the collar.

9. The device of claim 8, wherein the stimulator is configured to first apply magnetic stimulation, receive an outcome from the magnetic stimulation, and then apply electrical stimulation based on the received outcome.

10. The device of claim 9, wherein the received outcome is a reduction in patient hyperreflexia.

11. The device of claim 9, wherein the received outcome is a reduction in patient spasticity.

12. The device of claim 8, wherein the stimulator comprises a communication coil, and wherein the stimulator is configured to operate under telemetric control.

13. The device of claim 8, wherein the stimulating collar comprises a plastic magnetic conductance material.

14. The device of claim 8, wherein the stimulating collar comprises stimulating magnetic fibers.

* * * * *